United States Patent [19]

Fischer et al.

[11] Patent Number: 4,845,269

[45] Date of Patent: Jul. 4, 1989

[54] PREPARATION OF 3-PENTENOATES FROM 2-PENTENOATES

[75] Inventors: Rolf Fischer, Heidelberg; Wolfgang Hoelderich, Frankenthal; Manfred Sauerwald, Roedersheim-Gronau, all of Fed. Rep. of Germany

[73] Assignee: BASF Aktiengesellschaft, Ludwigshafen, Fed. Rep. of Germany

[21] Appl. No.: 125,560

[22] Filed: Nov. 25, 1987

[30] Foreign Application Priority Data

Nov. 27, 1986 [DE] Fed. Rep. of Germany ....... 3640596

[51] Int. Cl.$^4$ .............................................. C07C 69/52
[52] U.S. Cl. ..................................... 560/205; 560/211
[58] Field of Search ................................ 560/211, 205

[56] References Cited

U.S. PATENT DOCUMENTS

| | | | |
|---|---|---|---|
| 4,310,440 | 1/1982 | Wilson et al. | 252/435 |
| 4,339,592 | 7/1982 | Isogai et al. | 560/205 |
| 4,401,637 | 8/1983 | Marosi et al. | 423/329 |
| 4,440,871 | 4/1984 | Lok et al. | 502/214 |
| 4,473,663 | 8/1984 | Patton et al. | 502/208 |

FOREIGN PATENT DOCUMENTS

| | | |
|---|---|---|
| 103117 | 3/1984 | European Pat. Off. |
| 132708 | 2/1985 | European Pat. Off. |
| 2138450 | 6/1987 | European Pat. Off. |
| 266689 | 5/1988 | European Pat. Off. |
| 269046 | 6/1988 | European Pat. Off. |
| 2810031 | 9/1978 | Fed. Rep. of Germany |
| 3317163 | 11/1984 | Fed. Rep. of Germany |

OTHER PUBLICATIONS

Gronowitz, "Arkiv for Kemi", vol. 12, No. 25, pp. 243-244.
Advanced Organic Chemistry, McGraw-Hill, 1960, pp. 678-680.
Patent Abstract of Japan No. 56-29543, vol. 5, No. 79 (C-56) (751).
"Beilsteins Handbuch der Organischen Chemie", vol. II, pp. 426-427.
Journal of Organic Chemistry, vol. 33, p. 1971 (1968).
Tetrahedron Letters, vol. 25, p. 5181 (1984).
Canadian Journal of Chemistry, vol. 46, p. 2225 (1968).
J. Org. Chem. 1982, 47, pp. 2745-2748.
U.S. Ser. No. 06/826,760 (BASF) (OZ 37,596).

*Primary Examiner*—Paul J. Killos
*Attorney, Agent, or Firm*—Keil & Weinkauf

[57] ABSTRACT

3-pentenoates are prepared from 2-pentenoates by a process in which
(a) a 2-pentenoate of the formula

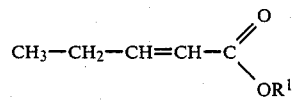

I where $R^1$ is alkyl of 1 to 12 carbon atoms, cycloalkyl of 5 to 8 carbon atoms, aralkyl of 7 to 10 carbon atoms or aryl of 6 to 10 carbon atoms, is reacted with a compound of the formula II

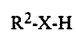

II where $R^2$ has the meanings given for $R^1$ and X is an oxygen or sulfur atom, or with a compound of the formula III

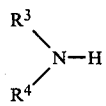

III where $R^3$ is hydrogen or $R^3$ and $R^4$ are each alkyl of 1 to 12 carbon atoms, cycloakkyl of 5 to 8 carbon atoms, aralkyl of 7 to 10 carbon atoms or aryl of 6 to 10 carbon atoms, and $R^3$ and $R^4$ together with the nitrogen atom on which they are substituents may form a 5-membered to 7-membered ring which may additionally contain a nitrogen or oxygen atom as a hetero atom, at from 20° to 300° C., in the presence or absence of a basic catalyst, to give a compound of the formula IV

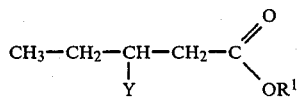

IV where Y is $-XR^2$ or

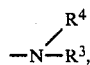

in which X, $R^1$, $R^2$, $R^3$ and $R^4$ have the above meanings, and
(b) the compound of the formula IV is cleaved in the liquid or gas phase in the presence of an acidic catalyst at from 150° to 450° C. to give a mixture of 3- and 2-pentenoates, and the 3-pentenoate is isolated.

20 Claims, No Drawings

PREPARATION OF 3-PENTENOATES FROM 2-PENTENOATES

J. Org. Chem. 33 (1968), 1971 et seq. discloses that 3-pentenoates are obtained by irradiating 2-pentenoates in the form of a 5% strength solution in pentane for five hours. Such a process cannot be carried out industrially; furthermore, large amounts of solvent have to be recovered. In another process, described in Tetrahedron Lett. 25 (1984), 5181 et seq., 2-alkenecarboxylates are converted to 3-alkenecarboxylates at −78° C. in tetrahydrofuran in the presence of potassium disilazide. Because of the low temperatures required and the expensive catalyst, this process cannot be carried out industrially. Furthermore, Can. J. Chem. 46 (1968), 2225 et seq. discloses a process in which methyl 2-trans-pentenoate is partially converted to methyl 3-pentenoate by heating at 259° C. for 328 hours. This process has the disadvantage that it is extremely time-consuming and requires considerable reaction spaces when carried out on an industrial scale.

It is an object of the present invention to provide a process for the preparation of 3-pentenoates from 2-pentenoates which takes place in a short time and can be carried out in a technically simple manner using readily available catalysts.

We have found that this object is achieved by a process for the preparation of 3-pentenoates from 2-pentenoates, wherein (a) a 2-pentenoate of the formula

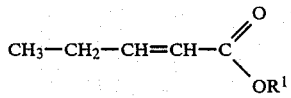
                            I where $R^1$ is alkyl of 1 to 12 carbon atoms, cycloalkyl of 5 to 8 carbon atoms, aralkyl of 7 to 10 carbon atoms or aryl of 6 to 10 carbon atoms, is reacted with a compound of the formula II $R^2$-X-H                            II where X is an oxygen or sulfur atom and $R^2$ has the meanings stated under $R^1$, or with a compound of the formula III

                            III where $R^3$ is hydrogen or $R^3$ and $R^4$ are each alkyl of 1 to 12 carbon atoms, cycloalkyl of 5 to 8 carbon atoms, aralkyl of 7 to 10 carbon atoms or aryl of 6 to 10 carbon atoms, or $R^3$ and $R^4$ together with the nitrogen atom on which they are substituents may form a 5-membered to 7-membered ring which may additionally contain a further nitrogen or oxygen atom, at from 20° to 300° C., in the presence or absence of a basic catalyst, to give a compound of the formula IV

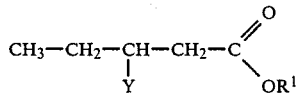
                            IV where Y is a radical $XR^2$ or

in which X, $R^1$, $R^2$, $R^3$ and $R^4$ have the above meanings, and (b) the compound of the formula IV is cleaved in the liquid or gas phase in the presence of an acidic catalyst at from 150° to 450° C. to give a mixture of 3- and 2-pentenoates, from which the 3-pentenoate is isolated.

The novel process has the advantages that it is easy to carry out industrially and takes place in a short time with good yields, and readily available catalysts are used.

The novel process is noteworthy in that the cleavage of the valerate substituted in the 3-position in the presence of an acidic catalyst was expected to result predominantly in the formation of 2-pentenoates. Furthermore, the formation of amides was expected in the reaction of the 2-pentenoates with amines.

In the 2-pentenoates of the formula I which are used as starting materials, $R^1$ is alkyl of 1 to 12 carbon atoms, such as methyl, ethyl, n-propyl, isopropyl, n-butyl, isobutyl, n-hexyl or n-decyl, cycloalkyl of 5 to 8 carbon atoms, such as cyclopentyl, cyclohexyl, cycloheptyl or cyclooctyl, aralkyl of 7 to 10 carbon atoms, such as benzyl or phenylethyl, and aryl of 6 to 10 carbon atoms, eg. phenyl or naphthyl. Examples of suitable starting compounds are methyl 2-pentenoate, ethyl 2-pentenoate, isopropyl 2-pentenoate, n-butyl 2-pentenoate, cyclohexyl 2-pentenoate, benzyl 2-pentenoate or phenyl 2-pentenoate. The stated pentenoates may be in the cis or trans form. Advantageously, $C_1$–$C_4$-alkyl 2-pentenoates are used as starting compounds. It is also possible to use mixtures of pentenoates which contain not only 2-pentenoates but also 3- and 4-pentenoates. In this case, 2- and 3-pentenoates are converted while the 4-pentenoate does not react and can be easily separated off.

The reaction is carried out using compounds of the formula II, where X is an oxygen or sulfur atom and $R^2$ has the same meanings as $R^1$. Examples of suitable compounds are methanol, ethanol, n-propanol, isopropanol, n-butanol, sec-butanol, n-pentanol, decanol, cyclohexanol, cyclopentanol, cycloheptanol, phenol, phenylethanol, methyl mercaptan and thiophenol. Alkanols of 1 to 4 carbon atoms have become particularly important.

In another procedure, the reaction is carried out using compounds of the formula III. In formula III, $R^3$ is hydrogen or $R^3$ and $R^4$ are each alkyl of 1 to 12 carbon atoms, cycloalkyl of 5 to 8 carbon atoms, aralkyl of 7 to 10 carbon atoms or aryl of 6 to 10 carbon atoms. $R^3$ and $R^4$ together with the nitrogen atom on which they are substituents may form a 5-membered to 7-membered ring which may also contain a further nitrogen or oxygen atom as a hetero atom. Examples of suitable compounds are methylamine, n-propylamine, sec-propylamine, n-butylamine, dimethylamine, diethylamine, di-n-butylamine, piperidine, morpholine, piperazine, pyrrolidine and azacycloheptane. Preferred compounds of the formula III are those in which $R^3$ is hydrogen or $R^3$ and $R^4$ are each alkyl of 1 to 4 carbon atoms, cyclohexyl or benzyl, or $R^3$ and $R^4$ together with the nitrogen atom on which they are substituents form a 5-membered to 7-membered ring which may contain a further oxygen or nitrogen atom as a hetero atom.

In the reaction of 2-pentenoates of the formula I with a compound of the formula II, it is advantageous if $R^1$ and $R^2$ are identical.

Whereas no catalysts are generally required for the reaction of 2-pentenoates I with compounds of the formula III, the reaction with compounds of the formula II is advantageously carried out in the presence of a basic catalyst.

Examples of suitable basic catalysts are alkali metal and alkaline earth metal hydroxides, such as lithium hydroxide, sodium hydroxide, potassium hydroxide, calcium hydroxide or barium hydroxide, alcoholates of alkali metals and of alkaline earth metals, in particular those of alkanols of 1 to 4 carbon atoms, such as sodium methylate, sodium ethylate or magnesium ethylate, aluminum alcoholates, titanium alcoholates and strongly basic ion exchangers, for example crosslinked polystyrene which contains amino groups, in particular quaternary amino groups. Other suitable catalysts are alkali metal and alkaline earth metal amides and hydrides, such as sodium amide, potassium amide, sodium hydride, potassium hydride of calcium hydride. Sodium alcoholates and potassium alcoholates of alkanols of 1 to 4 carbon atoms, strongly basic ion exchangers, amides and hydrides of sodium, potassium or calcium are particularly preferred.

The molar ratio of the 2-pentenoate I to the compounds of the formula II or III is advantageously from 1:0.5 to 1:10, in particular from 1:1 to 1:5.

The molar ratio of the pentenoate I to the basic catalysts is advantageously from 1:0.01 to 1:0.5, in particular from 1:0.05 to 1:0.2.

The reaction is carried out at from 20° to 300° C., preferably from 50° to 200° C. Advantageously, a temperature of from 40° to 95° C. is chosen for the reaction of 2-pentenoates I with compounds of the formula II. As a rule, the reaction is carried out under atmospheric pressure, although it is also possible to employ superatmospheric pressure, for example up to 10 bar. The reaction times are as a rule from 0.1 to 5, in particular from 1 to 2, hours.

The reaction may be carried out batchwise or continuously in the liquid phase, for example using a catalyst which is dissolved to give a homogeneous solution or suspended in the liquid phase, or a fixed-bed catalyst, for example by the liquid-phase or trickle-bed method. On the other hand, the reaction may also be carried out in the gas phase.

When the reaction is carried out batchwise, the procedure is, for example, as follows: the 2-pentenoate I is heated at the abovementioned temperature for the stated time with the above amounts of the comopund II in the presence of the basic catalyst described. If 2-pentenoates I are reacted with compounds of the formula III, the basic catalyst is dispensed with.

The reaction mixture is separated by distillation, if necessary after removal of the catalyst also used; for example by filtration, neutralization and extraction with water. In this procedure, excess compounds II or III and unconverted pentenoate isomers are separated off.

The reaction product obtained is a compound of the formula IV

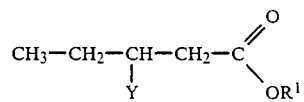

where Y is $-X-R^2$ or

in which X and $R^1$ to $R^4$ have the abovementioned meanings.

Examples are methyl 3-methoxyvalerate, ethyl 3-ethoxyvalerate, butyl 3-propoxyvalerate, cyclohexyl 3-cyclohexyloxyvalerate, benzyl 3-benzyloxyvalerate, methyl N-methyl-3-aminovalerate, butyl N-butyl-3-aminovalerate, methyl N-dimethyl-3-aminovalerate, methyl N-dibutyl-3-aminovalerate, ethyl N-cyclohexyl-3-aminovalerate, methyl N-benzyl-3-aminovalerate, methyl 3-piperidinovalerate, methyl 3-morpholinovalerate and methyl 3-piperazinovalerate.

In stage b), the compounds of the formula IV are cleaved in the liquid or gas phase in the presence of an acidic catalyst at from 150° to 450° C. to give a mixture of 3- and 2-pentenoates, from which the desired 3-pentenoate is isolated, for example by distillation. The compounds of the formulae II and III which are obtained as cleavage products, and 2-pentenoates and unconverted compounds of the formula IV, can be reused.

Examples of suitable acidic catalysts are acidic oxides of elements of main groups 3 to 5 and subgroups 4 to 6 of the Periodic Table. Silica in the form of silica gel, kieselguhr or quartz, and titanium dioxide, zirconium dioxide, phosphorus pentoxide, vanadium pentoxide, boron trioxide, alumina, chromium oxides, molybdenum oxides, tungsten oxides and mixtures of these are particularly preferred.

Zeolite catalysts are also particularly preferred. Zeolites are crystalline aluminosilicates whch have a highly ordered structure with a rigid three-dimensional network of $SiO_4$ and $AlO_4$ tetrahedra which are linked by common oxygen atoms. The ratio of Si and Al atoms to oxygen is 1:2. The electrovalency of the aluminum-containing tetrahedra is compensated by inclusion of cations in the crystal, for example alkali metal or hydrogen ions. Cation exchange is possible. The voids between the tetrahedra are occupied by water molecules prior to dehydration by drying or calcination.

In the zeolites, other trivalent and divalent elements, such as B, Ga, Fe, Cr, Be, As or Sb, can be incorporated in the structure in place of aluminum, or the silicon can be replaced by a tetravalent element, such as Ge, Ti, Zr or Hf.

Suitable catalysts are zeolites from the mordenite group or faujasite group, such as Y, X and L zeolites, or fine-pore zeolites of the erionite or chabasite type. Zeolites of the pentasil type are particularly advantageous for the novel process. These zeolites may have different chemical compositions. They are aluminosilicate, borosilicate, iron silicate, gallium silicate, chromium silicate, beryllium silicate, arsenic silicate, antimony silicate and bismuth silicate zeolites or mixtures of these, and aluminogermanate, borogermanate, gallium germanate and iron germanate zeolites or mixtures of these.

The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in 1,6-hexanediamine or 1,3-propanediamine or triethylenetetramine solution, with or, in particular, without the addition of an alkali or alkaline earth, at from 100° to 220° C. under autogenous pressure. These also include the isotactic zeolites according to German Laid-Open Application DOS No. 3,006,471. The resulting aluminosilicate zeolites have an $SiO_2/Al_2O_3$ ratio of from 10:1 to 40,000:1, depending on the amounts of starting materials chosen. Aluminosilicate zeolites of this type can also be synthesized in an ether medium, such as diethylene glycol dimethyl ether, in an alcoholic medium, such as methanol or butane-1,4-diol, or in water.

The borosilicate zeolite is synthesized, for example, at from 90° to 200° C. under autogenous pressure, by reacting a boron comopund, eg. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These also include the isotactic zeolites according to German Laid-Open Application DOS No. 3,006,471. Such borosilicate zeolites can also be prepared if the reaction is carried out in ether solution, for example diethylene glycol dimethyl ether, or in alcoholic solution, eg. hexane-1,6-diol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth, at from 100° to 200° C. under autogenous pressure.

The aluminosilicate, borosilicate and iron silicate zeolites thus prepared can be isolated, dried at from 100° to 160° C., preferably from 100° to 150° C., calcined at from 450° to 550° C., preferably from 500° to 540° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 95:5, preferably 75:25, silica, preferably finely divided $SiO_2$, mixtures of finely divided $SiO_2$ and finely divided $Al_2O_3$, and clay. After the molding procedure, the extrudates or pellets are dried at 110° C. for 16 hours and calcined at 500° C. for 16 hours.

Advantageous catalysts are also obtained if the aluminosilicate or borosilicate isolated is molded directly after drying and not subjected to calcination until after the molding procedure. The aluminosilicate and borosilicate zeolites prepared can be used in pure form, without a binder, as extrudates or pellets, the extrusion assistants or peptizing assistants used being, for example, ethylcellulose, stearic acid, potato starch, formic acid, oxalic acid, acetic acid, nitric acid, ammonia, amines, silicoesters or graphite or mixtures of these.

If, because of its method of preparation, the zeolite is not in the catalytically active, acidic form but, for example, in the Na form, the latter can be converted completely or partially to the desired H form by ion exchange, for example with ammonium ions, followed by calcination, or by treatment with an acid.

If, when the zeolite catalysts are used according to the invention, any deactivation occurs as a result of coking, it is advisable to regenerate the zeolites by burning off the coke deposit with air or with an air/$N_2$ mixture at from 400° to 550° C., preferably from 500° to 540° C. As a result, the zeolites regain their initial activity. By precoking, it is possible to adjust the activity of the catalyst to give optimum selectivity for the desired reaction product.

In order to obtain very high selectivity, a high conversion and a long life, it is sometimes advantageous to modify the zeolites with from 0.1 to 1% by weight of metals, for example those of subgroup VIII or group I. In a suitable method of modifying the catalysts, for example, the unmolded or molded zeolite is doped with metal salts by ion exchange or by impregnation.

Advantageously, doping is carried out, for example, as follows: the molded pentasil zeolite is initially taken in a riser tube, and, for example, an aqueous or ammoniacal solution of a halide or of a nitrate of the metals is passed over at from 20° to 100° C. Ion exchange of this kind can be carried out, for example, on the hydrogen, ammonium or alkali metal form of the zeolite. In another possible method of applying the metals to the zeolite, the zeolite material is impregnated with, for example, a halide, a nitrate or an oxide of the metals in aqueous, alcoholic or ammoniacal solution. Both ion exchange and impregnation are followed at least by drying, and if desired by repeated calcination.

In a possible embodiment, for example $Cs_2CO_3$ is dissolved in water and this solution is used to impregnate the molded or unmolded zeolite for a certain time (about 30 minutes). Any supernatant solution is freed from water in a rotary evaporator. Thereafter, the impregnated zeolite is dried at about 150° C. and calcined at about 550° C. This impregnation process can be carried out several times in succession in order to obtain the desired metal content.

It is also possible, for example, to prepare an ammoniacal $Pd(NO_3)_2$ solution and to suspend the pure powdered zeolite therein at from 40° to 100° C. for about 24 hours, while stirring. After being filtered off, dried at about 150° C. and calcined at about 500° C., the zeolite material thus obtained can be further processed with or without a binder to give extrudates, pellets or fluidizable material.

The zeolite in the H form can be subjected to ion exchange by initially taking the zeolite, in the form of extrudates or pellets, in a column and circulating, for example, an ammoniacal $Pd(NO_3)_2$ solution over the said zeolite at slightly elevated temperatures of from 30° to 80° C. for from 15 to 20 hours. The product is then washed thoroughly with water, dried at about 150° C. and calcined at about 550° C.

For some metal-doped zeolites, an aftertreatment with hydrogen is advantageous.

In another possible method of modification, the molded or unmolded zeolite material is subjected to a treatment with an acid, such as hydrochloric acid, hydrofluoric acid or phosphoric acid and/or steam.

Other catalysts for the preparation of 3-pentenoates from compounds of the formula IV are phosphates of the elements Al, B, Zr, Ce, Fe and mixtures of these.

Precipitated aluminum phosphates and in particular aluminum phosphates synthesized under hydrothermal conditions are used as aluminum phosphate catalysts for the novel process.

The aluminum phosphates prepared under hydrothermal conditions are, for example, APO-5, APO-9, APO-11, APO-12, APO-14, APO-21, APO-25, APO-31 and APO-33. Syntheses of these compounds are described in European Pat. No. 132,708 and U.S. Pat. Nos. 4,310,440 and 4,473,663.

For example, $AlPO_4$-5 (APO-5) is synthesized by mixing orthophosphoric aicd with pseudoboehmite in water to give a homogeneous mixture; tetrapropylammonium hydroxide is added to this mixture, and the reaction is then carried out at about 150° C. for from 20 to 60 hours under autogenous pressure in an autoclave. The $AlPO_4$-5 filtered off is dried at from 100° to 160° C. and calcined at from 450° to 550° C.

The silicon aluminum phosphates used for the novel process are, for example, SAPO-5, SAPO-11, SAPO-31 and SAPO-34. The synthesis of this compound is described, for example, in European Pat. No. 103,117 and U.S. Pat. No. 4,440,871. SAPOs are prepared by crystallization from an aqueous mixture at from 100° to 250° C. and under autogenous pressure in the course of from 2 hours to 2 weeks, the reaction mixture consisting of a silicon component, an aluminum component and a phosphorus component being reacted in an aqueous solution containing an organic amine.

The catalysts described here may alternatively be used in the form of 2–4 mm extrudates, pellets having a diameter of 3–5 mm or powders having particle sizes of from 0.1 to 0.5 mm, or as a fluidizable catalyst.

The reaction conditions generally chosen for the process according to the invention in the gas phase, which is preferred, are from 150° to 450° C., preferably from 180° to 300° C., and a WHSV or from 0.05 to 20 $h^{-1}$, preferably from 0.3 to 5 $h^{-1}$ (g of educt per g of catalyst per hour).

Sparingly volatile educts are used in dissolved form, for example in solution in tetrahydrofuran, toluene, methanol or petroleum ether. In general, dilution with solvents, for example those stated above, or inert gases such as $N_2$ or Ar is also possible.

An embodiment of the novel process in the gas phase is carried out, for example, as follows: the particular compound IV is first vaporized and then passed in gaseous form, if necessary together ith an inert gas, such as nitrogen, crabon dioxide or argon, at the above-mentioned reaction temperature, over a fixed-bed catalyst or a fluidized catalyst moving upward and downward. The reacted mixture is condensed using a suitable cooling apparatus and then worked up by fractional distillation. In this procedure, the desired 3-pentenoate is separated from the 2-pentenoate I and from any unconverted compound IV. The 2-pentenoates can be recycled to stage (a).

In another procedure, the reaction in stage (b) is carried out in the liquid phase, for example in a high boiling oil having a boiling range above the boiling points of the starting material IV and of the elimination products.

The cleavage reaction is effected, for example, by passing the compounds IV under the surface of an oil at above the boiling point of the elimination products. The elimination products and any unconverted starting material are removed in gaseous form, while some of the oil enriched with sparingly volatile byproducts is separated off and replaced with fresh oil, the oil separated off not being recovered but being fed to the undergrate firing for energy recovery. The reaction products obtained are mainly 3-pentenoates (cis and trans), and 2-trans-pentenoates, in addition to a little 4-pentenoate and 2-cis-pentenoate, are obtained as byproducts.

As a rule, high-boiling hydrocarbons which are inert under the reaction conditions, in particular appropriate mineral oil fractions having boiling ranges of from 300° to 550° C., are used as the reaction medium. Examples of suitable substances are vacuum gas oil, heavy fuel oil, vacuum residues, industrial white oil, marlotherm oil and molten paraffin wax.

The reaction temperatures are in general from 100° to 450° C., preferably from 150° to 350° C., in particular from 200° to 300° C., as a rule atmospheric pressure or reduced pressure being used. However, it is also possible to employ superatmospheric pressure.

The cleavage reaction is carried out in the presence of a catalyst. Suitable catalysts are both acidic compounds which are soluble in the reaction medium and those which are insoluble therein, the said compounds accordingly being present in dissolved, emulsified or suspended form. Aliphatic or aromatic sulfonic acids, such as benzenesulfonic acid, toluenesulfonic acid or dodecylbenzenesulfonic acid, inorganic acids, such as sulfuric acid, boric acid or phosphoric acid, or their partially esterified derivatives, and diphenylphosphinic acid and anhydrides, such as phosphorus pentoxide or boron oxide, are preferably used. Acidic catalysts on carriers, for example phosphoric acid on silica gel and alumina, aluminum phosphate, boron phosphate, aluminum silicate, heteropolyacids of phosphorus, molybdic acid and tungstic acid, are also suitable.

The catalysts are added to the high-boiling oil in amounts of from 0.01 to 25, preferably from 0.1 to 10, in particular from 1 to 5, % by weight.

The reaction is preferably carried out continuously. Examples of suitable reactors are stirred containers, cylindrical reactors or packed columns. These are advantageously up to $\frac{2}{3}$ filled with the oil used as reaction medium, to which a catalyst may have been added. The starting product is advantageously fed to the reactor from below, possibly with an inert gas, such as nitrogen, as a stripping gas. The reaction mixture is kept at the abovementioned reaction temperature, and the discharged products are condensed by cooling. The reaction products can be worked up by a conventional method, for example by distillation or extraction. Small amounts of sparingly volatile byproducts can be separated off by removing some of the reaction medium, the reactor content being supplemented, if necessary, with fresh oil. Working up and recycling the oil removed is, as a rule, not economical since the oils used are cheaply available. Advantageously, therefore, the oil separated off is fed for energy recovery by undergrate firing.

Compared with other known liquid-phase reactions, this novel process has the advantage that separation of substances is directly associated with the reaction, ie. the desired products are removed from the reaction medium at the rate at whichthey are formed, while sparingly volatile byproducts (crack products, polymers, etc.) remain behind in the oil. Because of the short residence times and low product concentration, side reactions are substantially suppressed. Furthermore, the process is simple to carry out industrially.

3-pentenoates are important intermediates, for example for the preparation of adipic acid and caprolactam.

EXAMPLE 1

In a 500 ml three-necked flask, 228 g of methyl 2-trans-pentenoate were mixed with a solution of 5.4 g of sodium methylate in 320 g of methanol (molar ratio 1:0.05:5) at room temperature, and the mixture was heated to 65° C. and stirred at this temperature for 4 hours. After the mixture had cooled, the sodium methylate was neutralized with glacial acetic acid, the methanol was substantially distilled off under atmospheric pressure, and the residue was then subjected to fractional distillation. This gave 211.9 g (73% of theory) of methyl 3-methoxyvalerate of boiling point 121°–126° C./302 mbar. 40.1 g of unconverted methyl 2-pentenoate and 4.6 g of distillation residue were also obtained.

EXAMPLE 2

When methyl 2-cis-pentenoate was used instead of methyl 2-trans-pentenoate, and 57.7 g of methyl 2-cis-pentenoate, 1.35 g of sodiummethylate and 80 g of methanol were employed under the reaction conditions and working-up conditions of Example 1, 44.2 g (61% of theory) of methyl 3-methoxyvalerate of boiling point 123°–128° C./300 mbar were obtained. 17.6 g of methyl 2-pentenoate was also obtained. The distillation residue was 1.5 g.

EXAMPLE 3

When Example 1 was repeated with 5.6 g of KOH instead of 5.4 g of sodium methylate, and the reaction conditions and working-up conditions of Example 1 were employed, 100.9 g (35% of theory) of methyl 3-methoxyvalerate of boiling point 122°–125° C./304 mbar and 131.1 g (58% of theory) of methyl pentenoate were obtained.

EXAMPLE 4

56 g of a strongly basic ion exchanger (OH form, methanol-moist) were suspended in a mixture of 100 g of methyl pentenoate (85% of methyl 2-trans-pentenoate, 5% of methyl 2-cis-pentenoate and 10% of methyl 3-pentenoate) and 140 g of methanol. The mixture was heated to 65° C. and then stirred for 3 hours at this temperature. After this time, analysis by gas chromatography showed that the reaction mixture (without methanol) consisted of 80.3% of methyl 3-methoxyvalerate and 18.8% of pentenoates (12% of methyl 2-trans-pentenoate, 0.5% of methyl 2-cis-pentenoate and 6.3% of methyl 3-pentenoate) (percentages by area). Fractional distillation gave 93.4 g (73% of theory) of methyl 3-methoxyvalerate of boiling point 128° C./302 mbar and 15.3 g (15% of theory) of methyl pentenoate.

EXAMPLE 5

A solution of 0.81 g of sodium methylate in 17.1 g of methyl 2-trans-pentenoate and 16.5 g of thiophenol was heated at 65° C. for 2 hours. After this time, analysis by gas chromatography indicated 82% of methyl 3-thiophenoxyvalerate, 8% of thiophenol and 4% of methyl 2-trans-pentenoate. 15.2 g (45% of theory) of methyl 3-thiophenoxyvalerate having a boiling point of about 100° C./1 mbar were obtained by distillation.

EXAMPLE 6

A mixture of 500 g of methyl 2-trans-pentenoate and 372 g of piperidine was heated at 100° C. for 24 hours. 562 g (64% of theory) of methyl 3-piperidinovalerate of boiling point 75°–77° C./2 mbar were obtained by fractional distillation.

EXAMPLE 7

0.024 g of sodium methylate in 1.4 g of methanol was added to a mixture of 9 g of methyl 4-cis-pentenoate and 1 g of methyl 2-cis-pentenoate, and the mixture was heated at 100° C. for 3 hours. According to analysis by gas chromatography, after this time the reaction mixture consisted of 89.3% of methyl 4-pentenoate, 0.2% of methyl 2-cis-pentenoate, 3.3% of methyl 2-trans-pentenoate, 2% of methyl 3-pentenoate and 5.1% of methyl 3-methoxyvalerate. This example shows that methyl 4-pentenoate remains unchanged whereas the 2-pentenoate is converted.

EXAMPLE 8

10 g/hour of methyl 3-methoxyvalerate were pumped into an evaporator and passed from there, in gaseous form together with 3 l of nitrogen, at 300° C., over 5 g of an $Al_2O_3$ catalyst. The gaseous reaction products were condensed, weighed and analysed by gas chromatography. In the course of a reaction time of 6 hours, 49 g of reacted mixture consisting of 37% of methyl 3-pentenoate, 33% of methyl 2-trans-pentenoate, 5% of methyl 2-cis-pentenoate, 1% of methyl 4-pentenoate and 22% of unconverted methyl 3-methoxyvalerate were obtained. The ratio of 3-pentenoates to 2-pentenoates was accordingly 1:1.

EXAMPLE 9

10 g/hour of methyl 3-methoxyvalerate were pumed into an evaporator and passed from there, in gaseous form together with 3 l of nitrogen, at 350° C., over 5 g of an $SiO_2$ catalyst. The gaseous reaction products were condensed, weighed and analysed by gas chromatography. In the course of 6 hours, 53.3 g of the reacted mixture consisting of 30% of methyl 3-pentenoate, 56% of methyl 2-transpentenoate, 8% of methyl 2-cis-pentenoate, 2% of methyl 4-pentenoate and 3% of unconverted methyl 3-methoxyvalerate were obtained. The ratio of 3-pentenoates to 2-pentenoates was accordingly 1:2.2.

EXAMPLE 10

As described in Example 9, 10 g of methyl piperidinovalerate from a) were passed over 5 g of alumina at 300° C. The reacted mixture consisted of 10% of methyl 3-pentenoate, 24% of methyl 2-pentenoate, 8% of starting material and 16% of unknown compounds.

The preparation of zeolites which have been used for the cleavage of methyl 3-methoxyvalerate is described in Examples 11 to 15.

EXAMPLE 11

Catalyst A

The aluminosilicate zeolite of the pentasil type was prepared under hydrothermal conditions, under autogenous pressure and at 150° C., from 650 g of finely divided $SiO_2$ and 203 g of $Al_2(SO_4)_3 \cdot 18\ H_2O$ in 10 kg of an aqueous 1,6-hexanediamine solution (weight ratio 50:50) in a stirred autoclave. The crystalline reaction product was filtered off, washed thoroughly, dried at 110° C. for 24 hours and calcined at 500° C. for 24 hours. This aluminosilicate zeolite contained 92.8% by weight of $SiO_2$ and 4.2% by weight of $Al_2O_3$.

Catalyst A is obtained by molding the pure aluminosilicate zeolite of the pentasil type with molding assistants to give 2 mm extrudates and drying the latter at 110° C. for 16 hours and calcining them at 500° C. for 24 hours.

EXAMPLE 12

Catalyst B

The borosilicate zeolite of the pentasil type was prepared in a hydrothermal synthesis from 640 g of finely divided $SiO_2$, 122 g of $H_3BO_3$ and 8 kg of an aqueous 1,6-hexanediamine solution (weight ratio 50:50) at 170° C. under autogenous pressure in a stirred autoclave. The crystalline reaction product was filtered off, washed thoroughly, dried at 100° C. for 24 hours and calcined at 500° C. for 24 hours. This borosilicate zeolite was com-posed of 94.2% by weight of $SiO_2$ and 2.3% by weight of $B_2O_3$.

This material was molded with molding assistants to give 2 mm extrudates, which were dried at 110° C. for 16 hours and calcined at 500° C. for 24 hours.

EXAMPLE 13

Catalyst C

Catalyst C was obtained by impregnating catalyst B with aqueous $Cs_2CO_3$ solution. After the product had been dried at 130° C. for 2 hours and calcined at 540° C. for 2 hours, the Cs content was 0.6% by weight.

EXAMPLE 14

Catalyst D

Catalyst D was obtained by molding the aluminosilicate zeolite of catalyst A with boehmite in a weight ratio of 60:40 and drying the product at 110° C. and calcining it at 500° C. for 16 hours. The resulting extrudates were impregnated with aqueous LiOH solution. After the product had been dried at 130° C. for 2 hours and calcined at 540° C. for 2 hours, the Li content was 0.9% by weight.

EXAMPLE 15

Catalyst E

Commercial Na-Y zeolite was subjected to ion exchange with aqueous $(NH_4)_2SO_4$ solution by a known method until the Na content was less than 0.5% by weight (after drying at 110° C. for 2 hours and calcination at 570° C. for 3 hours).

The resulting powder was molded with molding assistants to give extrudates, which were dried at 110° C. and calcined at 500° C. for 16 hours.

EXAMPLES 16 TO 22

Examples 16 to 22 were carried out under isothermal conditions in a tube reactor (diameter 0.6 cm, length 90 cm) in the gas phase using a zeolite as the catalyst. Methyl 3-methoxyvalerate prepared as described in a) was used. Tetrahydrofuran or methanol was used as the solvent. The reaction products were analysed by gas chromatography (Table).

EXAMPLE 23

A 1 l stirred flash was charged with 500 g of vacuum gas oil and 6 g of an 85% strength phosphoric acid, and the mixture was heated to 300° C. 40 g/hour of methyl 3-methoxyvalerate from a stock vessel were fed, together with 10 l/hour of nitrogen, below the surface of the stirred oil/catalyst mixture. The gaseous products leaving the reaction vessel were cooled, and the condensate was investigated by gas chromatography. In this manner, 11.0 g/hour of methyl 3-pentenoate and 10.7 g/hour of 2-trans-pentenoate were obtained, inter alia, in addition to 7.5 g/hour of unconverted methyl 3-methoxyvalerate.

TABLE

| Cleavage of methyl 3-methoxyvalerate (3-MVAE) over zeolites | | | | | | | |
|---|---|---|---|---|---|---|---|
| Example | 16 | 17 | 18 | 19 | 20 | 21 | 22 |
| Educt[1] | I | I | I | II | II | II | II |
| Catalyst | B | D | E | A | C | E | E |
| Temperature | 300° C. | 300° C. | 180° C. | 180° C. | 300° C. | 180° C. | 300° C. |
| WHSV | $2\,h^{-1}$ | $2\,h^{-1}$ | $2.5\,h^{-1}$ | $2.6\,h^{-1}$ | $3.6\,h^{-1}$ | $2.8\,h^{-1}$ | $2.3\,h^{-1}$ |
| Reacted mixture containing, in % by weight: | | | | | | | |
| 3-PAE[2] | 42.9 | 46.2 | 44 | 40.6 | 38.7 | 45.3 | 44.7 |
| 2-trans-PAE | 34.4 | 28.0 | 10.5 | 24.5 | 36.5 | 12.2 | 28.0 |
| 2-cis-PAE | 7.1 | 6.5 | 1.6 | 4.7 | 12.0 | 1.7 | 8.7 |
| 4-PAE | 8.6 | 9.9 | 5.5 | 7.9 | 5.9 | 5.7 | 8.3 |
| 5-methyl butyrolactone | 5.6 | 3.9 | 19.3 | 7.3 | 1.0 | 17.8 | 4.4 |
| 3-MVAE | / | / | 18.4 | 13.9 | 5.8 | 16.2 | 5.2 |

[1]I: 3-MVAE to THF = 1:1 (% by weight); II: 3-MVAE to $CH_3OH$ = 1:1 (% by weight)
[2]PAE = methyl pentenoate

We claim:

1. A process for the preparation of a 3-pentenoate from a 2-pentenoate comprising (a) reacting a 2-pentenoate of the formula I

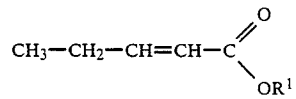

I where $R^1$ is alkyl of 1 to 12 carbon atoms, cycloalkyl of 5 to 8 carbon atoms, aralkyl of 7 to 10 carbon atoms or aryl of 6 to 10 carbon atoms, with a compound of the formula II $R^2\text{-X-H}$  II where $R^2$ has the meanings given for $R^1$ and X is an oxygen or sulfur atom, or with a compound of the formula III,

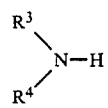

III where $R^3$ is hydrogen or $R^3$ and $R^4$ are each alkyl of 1 to 12 carbon atoms, cycloalkyl of 5 to 8 carbon atoms, aralkyl of 7 to 10 carbon atoms or aryl of 6 to 10 carbon atoms, and $R^3$ and $R^4$ together with the nitrogen atom on which they are substituents may form a 5-membered to 7-membered ring which may additionally contain a nitrogen or oxygen atom as a hetero atom, at from 20° to 300° C., in the presence or absence of a basic catalyst, to give a compound of the formula IV

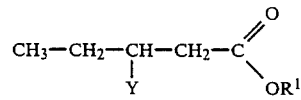

IV where Y is -$XR^2$ or

in which X, $R^1$, $R^2$, $R^3$ and $R^4$ have the above meanings, (b) cleaving the compound of the formula IV in the liquid or gas phase in the presence of an acidic catalyst at from 150 to 450° C. to give a mixture of 3- and 2-pentenoates, and (c) isolating the 3-pentenoate.

2. The process of 1, wherein, in the reaction of a 2-pentenoate of the formula I with a compound of the formula II, an alkali metal or alkaline earth metal hydroxide, an alkali metal alcoholate or a strongly basic ion exchanger is used as the catalyst and the reaction is carried out at from 40° to 95° C.

3. The process of claim 1, wherein from 1 to 5 moles of a compound of the formula II or III is used per mole of 2-pentenoate of the formula I.

4. The process of claim 1, wherein, in stage (b), alumina, boron trioxide, titanium dioxide, silica, a zeolite or a phosphate or a mixture of these is used as the catalyst.

5. The process of claim 1, wherein, in stage (b), a zeolite of the faujasite type is used as the catalyst.

6. The process of claim 1, wherein, in stage (b), an aluminosilicate zeolite of the pentasil type is used as the catalyst.

7. The process of claim 1, wherein, in stage (b), a borosilicate zeolite of the pentasil type is used as the catalyst.

8. The process of claim 1, wherein, in stage (b), an iron silicate zeolite of the pentasil type is used as the catalyst.

9. The process of claim 1, wherein, in stage (b), an aluminum phosphate, a silicon aluminum phosphate, an iron silicon phosphate or a boron phosphate or a mixture of these is used as the catalyst.

10. The process of claim 1, wherein, in stage (b), a zeolite which is doped with alkali, alkaline earth or transition metals or rare earth metals or a mixture of these is used as the catalyst.

11. The process of claim 1, wherein, in stage (b), a compound of the formula IV is cleaved in a highboiling oil at above the boiling point of the particular compound of the formula IV employed and its cleavage products, the reaction products are removed in gaseous form, and some of the oil containing sparingly volatile byproducts is separated off and replaced with fresh oil.

12. The process of claim 11, wherein a mineral oil having a boiling point of from 300° to 550° C. is used as the high-boiling oil.

13. The process of claim 11, wherein vacuum gas oil, heavy fuel oil, vacuum residue, industrial white oil or molten paraffin wax is used as the high-boiling oil.

14. The process of claim 11, wherein the reaction is carried out under atmospheric pressure and/or under reduced pressure.

15. A process for the preparation of a 3-pentenoate from a 2-pentenoate comprising (a) reacting a 2-pentenoate of the formula I

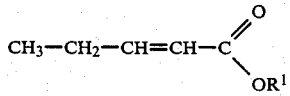

where $R^1$ is alkyl of 1 to 12 carbon atoms, cycloalkyl of 5 to 8 carbon atoms, aralkyl of 7 to 10 carbon atoms or aryl of 6 to 10 carbon atoms, with a compound of the formula II $R^2$-X-H          II where $R^2$ has the meanings given for $R^1$ and X is an oxygen or sulfur atom, at from 20° to 300° C., in the presence of a basic catalyst, to give a compound of the formula IV

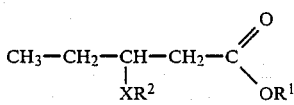

in which X, $R^1$ and $R^2$ have the above meanings, (b) cleaving the compound of the formula IV in the liquid or gas phase in the presence of an acidic catalyst at from 150° to 450° C. to give a mixture of 3- and 2-pentenoates, and (c) isolating the 3-pentenoate.

16. The process of claim 15, wherein, in stage b), alumina, boron trioxide, titanium dioxide, silica, a zeolite or a phosphate or a mixture of these is used as the catalyst.

17. The process of claim 15, wherein, in stage b), the compound of the formula IV is cleaved in the gas phase.

18. A process for the preparation of a 3-pentenoate from a 2-pentenoate comprising (a) reacting a 2-pentenoate of the formula I

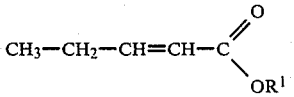

where $R^1$ is alkyl of 1 to 12 carbon atoms, cycloalkyl of 5 to 8 carbon atoms, aralkyl of 7 to 10 carbon atoms or aryl of 6 to 10 carbon atoms, with a compound of the formula III

where $R^3$ is hydrogen or $R^3$ and $R^4$ are each alkyl of 1 to 12 carbon atoms, cycloalkyl of 5 to 8 carbon atoms, aralkyl of 7 to 10 carbon atoms or aryl of 6 to 10 carbon atoms, and $R^3$ and $R^4$ together with the nitrogen atom on which they are substituents may form a 5-membered to 7-membered ring which may additionally contain a nitrogen or oxygen atom as a hetero atom, at from 20° to 300° C., to give a compound of the formula IV

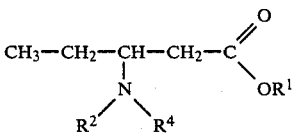

in which $R^1$, $R^3$ and $R^4$ have the above meanings, (b) cleaving the compound of the formula IV in the liquid or gas phase in the presence of an acidic catalyst at from 150° to 450° C. to give a mixture of 3- and 2-pentenoates, and (c) isolating the 3-pentenoate.

19. The process of claim 18, wherein, in stage b), alumina, boron trioxide, titanium dioxide, silica, a zeolite or a phosphate or a mixture of these is used as the catalyst.

20. The process of claim 18, wherein, in stage b), the compound of the formula IV is cleaved in the gas phase.

* * * * *